United States Patent
Suzuki et al.

(10) Patent No.: US 10,952,626 B2
(45) Date of Patent: Mar. 23, 2021

(54) PULSEBEAT MEASUREMENT APPARATUS

(71) Applicant: KDDI CORPORATION, Tokyo (JP)

(72) Inventors: Masahiro Suzuki, Fujimino (JP); Tomoaki Ueda, Tokyo (JP)

(73) Assignee: KDDI CORPORATION, Tokyo (JP)

( * ) Notice: Subject to any disclaimer, the term of this patent is extended or adjusted under 35 U.S.C. 154(b) by 304 days.

(21) Appl. No.: 16/032,835

(22) Filed: Jul. 11, 2018

(65) Prior Publication Data
US 2018/0317790 A1    Nov. 8, 2018

Related U.S. Application Data

(63) Continuation of application No. PCT/JP2016/086012, filed on Dec. 5, 2016.

(30) Foreign Application Priority Data

Jan. 26, 2016  (JP) .............................. JP2016-012254

(51) Int. Cl.
*A61B 5/024* (2006.01)
*A61B 5/0245* (2006.01)
(Continued)

(52) U.S. Cl.
CPC ............ *A61B 5/02444* (2013.01); *A61B 5/01* (2013.01); *A61B 5/0245* (2013.01);
(Continued)

(58) Field of Classification Search
CPC ... A61B 5/02444; A61B 5/01; A61B 5/02055; A61B 5/02416; A61B 5/02438;
(Continued)

(56) References Cited

U.S. PATENT DOCUMENTS 5,018,872 A    5/1991  Suszynski et al.
6,909,271 B2 *  6/2005  Sloneker ................ G01K 7/021
                                                   324/117 R
(Continued)

FOREIGN PATENT DOCUMENTS

JP        57-045907 U    3/1982
JP       S57-045907 U    3/1982
(Continued)

OTHER PUBLICATIONS

English Translation of Sugai, Japanese Utility Model Laid-Open No. S57-45907 (Year: 1980).*
(Continued)

*Primary Examiner* — David J McCrosky
*Assistant Examiner* — Chanel J Jhin
(74) *Attorney, Agent, or Firm* — Fitch, Even, Tabin & Flannery LLP

(57) ABSTRACT

There is provided a pulsebeat measurement apparatus. The pulsebeat measurement apparatus includes a first temperature detector configured to detect a temperature of a human body, a specifying unit configured to specify a period of a temperature change caused by a pulsation of the human body based on the detected temperature, a pulsebeat measurement unit configured to measure a pulsebeat of the human body based on the specified period of the temperature change, and a heat absorber configured to absorb heat of the first temperature detector.

6 Claims, 3 Drawing Sheets

(51) Int. Cl.
*A61B 5/00* (2006.01)
*A61B 5/01* (2006.01)
*A61B 5/0205* (2006.01)

(52) U.S. Cl.
CPC ...... *A61B 5/02055* (2013.01); *A61B 5/02416* (2013.01); *A61B 5/02438* (2013.01); *A61B 5/681* (2013.01); *A61B 5/7278* (2013.01); *A61B 5/6815* (2013.01); *A61B 2562/0271* (2013.01)

(58) Field of Classification Search
CPC ..... A61B 5/0245; A61B 5/681; A61B 5/7278; A61B 5/6815; A61B 2562/0271; A61B 2562/04; A61B 2560/0214; A61B 5/441; A61B 5/6804; A61B 2562/18
USPC ........................................................ 600/500
See application file for complete search history.

(56) References Cited

U.S. PATENT DOCUMENTS

| | | | |
|---|---|---|---|
| 9,500,535 | B1 | 11/2016 | Urban et al. |
| 2002/0008042 | A1 | 1/2002 | Pierro, Jr. et al. |
| 2002/0143257 | A1 | 10/2002 | Newman et al. |
| 2003/0171655 | A1 | 9/2003 | Newman et al. |
| 2004/0102914 | A1 | 5/2004 | More |
| 2004/0167381 | A1 | 8/2004 | Lichter et al. |
| 2005/0152146 | A1 | 7/2005 | Owen et al. |
| 2007/0295713 | A1* | 12/2007 | Carlton-Foss ........... A61B 5/01 219/497 |
| 2010/0062683 | A1 | 3/2010 | Brundage |
| 2015/0126896 | A1 | 5/2015 | Alhazme |
| 2016/0183794 | A1 | 6/2016 | Gannon et al. |
| 2016/0262694 | A1 | 9/2016 | Calcano et al. |
| 2016/0310112 | A1 | 10/2016 | Gevaert et al. |
| 2018/0263508 | A1 | 9/2018 | Yoshihiko et al. |

FOREIGN PATENT DOCUMENTS

| | | |
|---|---|---|
| JP | H04-501611 A | 3/1992 |
| JP | H08-266491 A | 10/1996 |
| JP | 2001-000422 A | 1/2001 |
| JP | 2004-528085 A | 9/2004 |
| JP | 2005-519666 A | 7/2005 |
| JP | 2006-102161 A | 4/2006 |
| JP | 3819877 B2 | 9/2006 |
| JP | 2008-245943 A | 10/2008 |
| JP | 2009-279076 A | 12/2009 |
| JP | 2010-264095 A | 11/2010 |
| JP | 2011-133300 A | 7/2011 |
| JP | 2014-139585 A | 7/2014 |
| WO | 2007-138699 A1 | 12/2007 |
| WO | 2014157138 A1 | 10/2014 |
| WO | 2016111261 A1 | 7/2016 |

OTHER PUBLICATIONS

JPO; Application No. 2016-012254; Office Action dated Feb. 26, 2019.
"Regarding Development and Practical Use of "hitoe" Which Is a Functional Material That Enable Biometric Information to Be Continuous Measured Just by Wearing It", Internet [URL: https://www.nttdocomo.co.jp/info/news_release/2014/01/30_00.html], <search on Jun. 5, 2015>.
PCT; App. No. PCT/JP2016/086012; International Search Report dated Jan. 24, 2017.
Philip, James et al., "Continuous Thermal Measurement of Cardiac Output," IEEE Transactions on Biomedical Engineering, May 1984, pp. 393-400, vol. BME-31, No. 5.

* cited by examiner

PULSEBEAT MEASUREMENT APPARATUS

This application is a continuation of International Patent Application No. PCT/JP2016/086012 filed on Dec. 5, 2016, and claims priority to Japanese Patent Application No. 2016-012254 filed on Jan. 26, 2016, the entire content of both of which is incorporated herein by reference.

TECHNICAL FIELD

The present invention relates to a pulsebeat measurement apparatus.

BACKGROUND ART

In recent years, a computer (so-called wearable device) such as a wristwatch, ring, or a pair of glasses which can be directly worn and carried by the user is attracting attention. There is no big difference between simply wearing and carrying a small computer. Therefore, an application technique which makes the best use of a feature of always wearing is required for the wearable device. As such application technique, a vital sensing technique of automatically recording the condition of the user at the time of wearing is plausible. An example of the vital sensing technique is pulsebeat measurement.

In general, as pulsebeat measurement, electrocardiography of detecting a heart rate almost equivalent to a pulse rate using the peaks, for example, P waves, R waves, or the like of an electrocardiographic waveform measured by attaching electrodes to a living body, photoplethysmography of irradiating a peripheral blood vessel such as a wrist, finger, or earlobe with light, and detecting a pulsebeat based on an optical change in which reflected light periodically changes due to a blood flow and light absorption characteristic, and the like have been widely used.

NPL 1 discloses an apparatus capable of performing heart beat measurement by embedding, in clothing, a measurement electrode according to a sport electrocardiographic lead system, and wearing it. Furthermore, PTL 1 discloses an arrangement capable of measuring a heart beat by wearing, on a pinna, an apparatus including a sensor for performing irradiation with an infrared ray.

CITATION LIST

Patent Literature

PTL 1: Japanese Patent Laid-Open No. 2006-102161

Non Patent Literature

NPL 1: "Regarding Development and Practical Use of "hitoe" Which Is a Functional Material That Enable Biometric Information to Be Continuous Measured Just by Wearing It", Internet [URL: http s://www.nttdocomo.co.jp/info/news_release/2014/01/30_00 html], <search on Jun. 5, 2015>

SUMMARY OF THE INVENTION

Technical Problem

The apparatus disclosed in NPL 1 (electrocardiography) can measure a heart beat correctly since the electrode is worn on the body surface. Since, however, it is necessary to bring the electrode into tight contact with the human body, he/she has an unwell feeling such as a restraint feeling or oppressive feeling. In addition, it is necessary to wash the clothing, and the washing count is limited in terms of durability, thereby impairing the usability.

In the apparatus disclosed in NPL 1, the power consumption of a light emitting element is large. Therefore, for example, if the apparatus is used for a small terminal apparatus such as a wearable device, it is impossible to continuously measure a pulsebeat all the time. In addition, if the user has a tattoo or the like, a coloring matter blocks light, and thus it may be impossible to capture reflected light appropriately.

To solve the above problems, the present inventors propose a wearable pulsebeat measurement apparatus that measures a pulsebeat by specifying occurrence of an instantaneous small change in body temperature of a human body caused by a pulsation in addition to a gradual change in body temperature in daily life, and detecting a small change in temperature caused by a pulsation using a temperature sensor that detects the temperature on a contact surface with the human body. Since, for example, it is only necessary to cause the temperature sensor to contact a wrist, an ankle, or the like, and very low power is required to detect the temperature, the pulsebeat measurement apparatus can be downsized and a pulsebeat can be measured at low power.

However, if the pulsebeat measurement apparatus is downsized, the total heat capacity of the pulsebeat measurement apparatus becomes small. Consequently, when detecting the body temperature of the human body using the temperature sensor, a state unwantedly transits to the thermal equilibrium state within a short time, and it is thus impossible to accurately detect a small change in temperature caused by a pulsation.

Solution to Problem

According to one aspect of the present invention, a pulsebeat measurement apparatus includes: a first temperature detector configured to detect a temperature of a human body; a specifying unit configured to specify a period of a temperature change caused by a pulsation of the human body based on the detected temperature; a pulsebeat measurement unit configured to measure a pulsebeat of the human body based on the specified period of the temperature change; and a heat absorber configured to absorb heat of the first temperature detector.

Other features and advantages of the present invention will be apparent from the following description taken in conjunction with the accompanying drawings. Note that the same reference numerals denote the same or like components throughout the accompanying drawings.

DESCRIPTION OF THE EMBODIMENTS

First Embodiment

Figure 1:
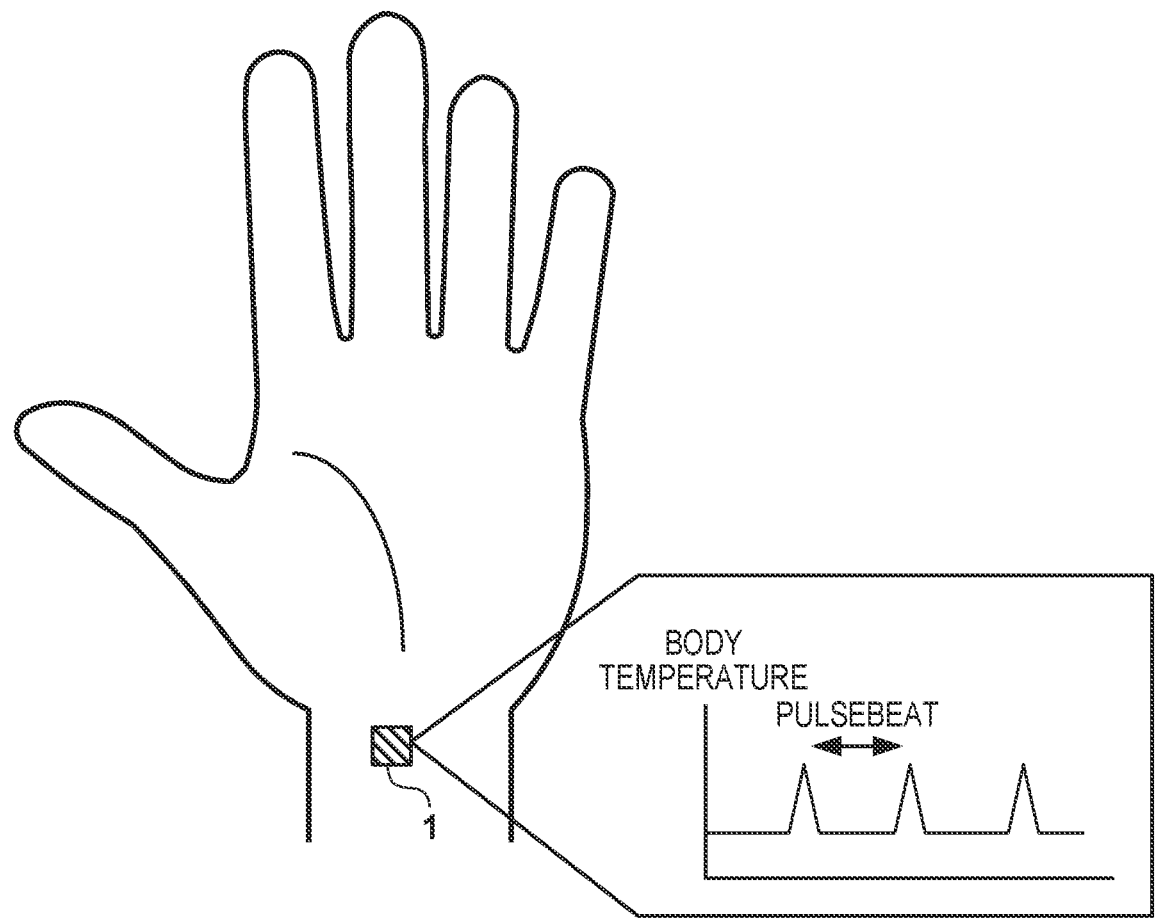
FIG. 1 is a view for explaining a pulsebeat measurement method by a pulsebeat measurement apparatus.

An outline of a pulsebeat measurement apparatus 1 according to this embodiment will be described first with reference to FIG. 1. FIG. 1 is a view for explaining a pulsebeat measurement method by the pulsebeat measurement apparatus 1 according to this embodiment. As shown in FIG. 1, the pulsebeat measurement apparatus 1 detects a small change in body temperature in an arbitrary portion (for example, a wrist, neck, ankle, or the like) of a human body, and measures a pulsebeat based on the period of the small change in body temperature. For example, by providing the pulsebeat measurement apparatus 1 in each of various wearable devices such as a wristwatch type device and a spectacles type device, it is possible to measure the pulse rate of the user wearing the wearable device.

Figure 2:
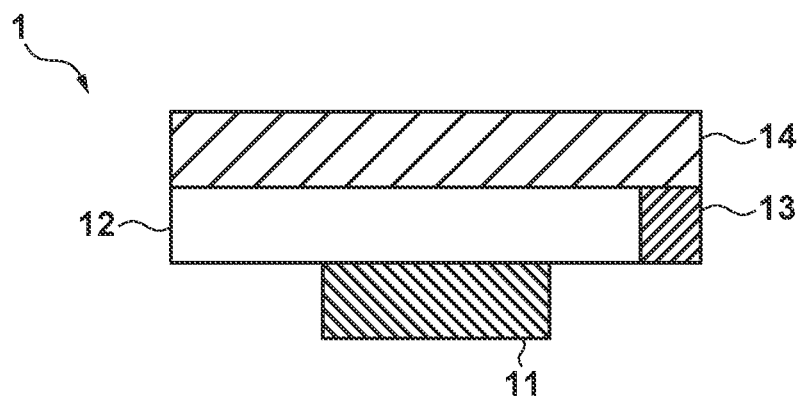
FIG. 2 is a view showing the arrangement of the pulsebeat measurement apparatus according to an embodiment.
Figure 3:
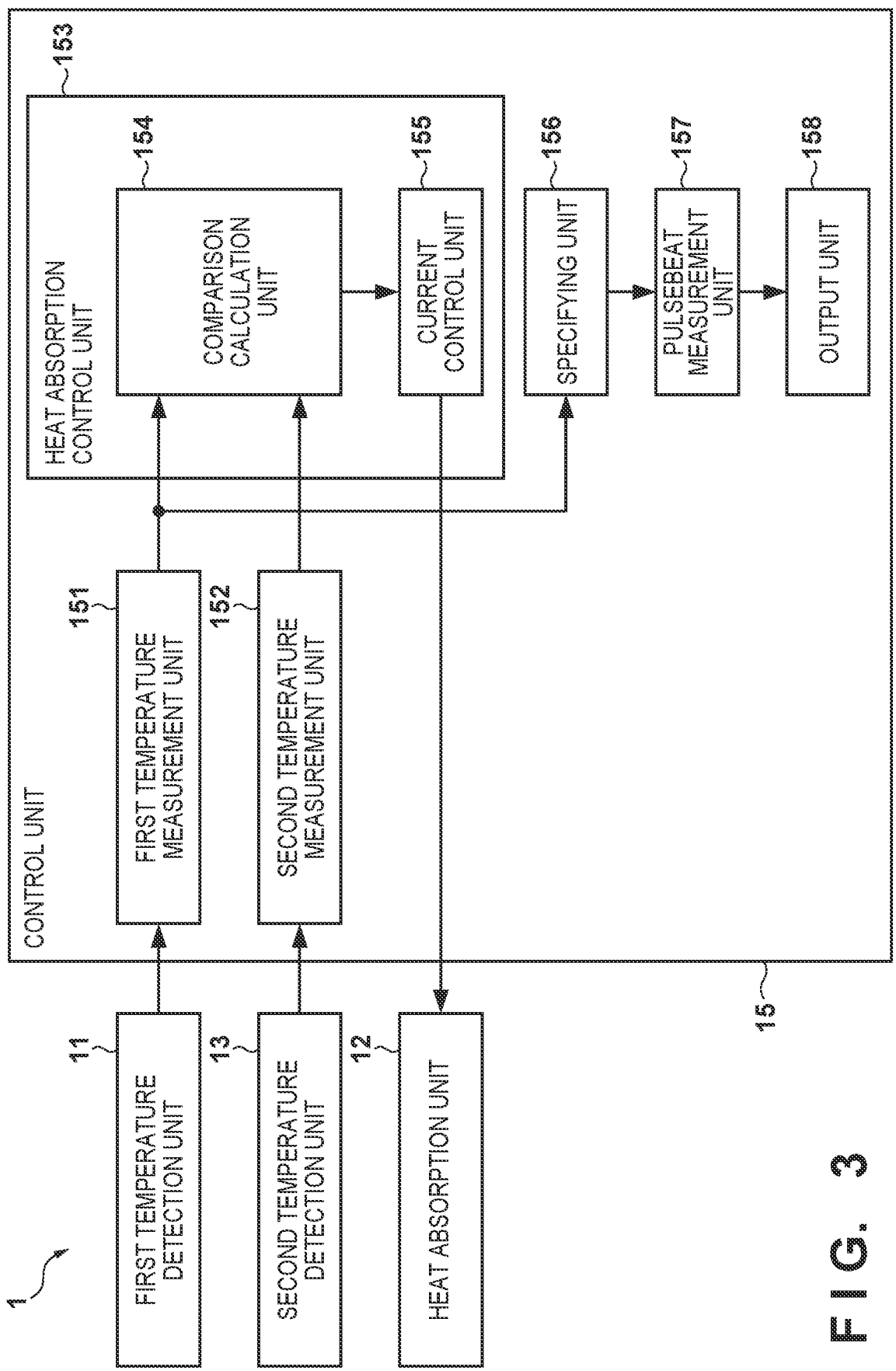
FIG. 3 is a block diagram showing the arrangement of a control unit provided in the pulsebeat measurement apparatus according to an embodiment.

FIG. 2 is a view showing the arrangement of the pulsebeat measurement apparatus 1 according to this embodiment. FIG. 3 is a block diagram showing the arrangement of a control unit 15 provided in the pulsebeat measurement apparatus 1 according to this embodiment. As shown in FIGS. 2 and 3, the pulsebeat measurement apparatus 1 includes a first temperature detection unit 11, a heat absorption unit 12, a second temperature detection unit 13, a heat dissipation unit 14, and the control unit 15.

The first temperature detection unit 11 includes a resistance temperature detector, such as a thermistor-type resistance temperature detector or platinum resistance temperature detector whose resistance value changes in accordance with a change in temperature, and a lead wire for causing a current to flow into the resistance temperature detector. The first temperature detection unit 11 detects the temperature of a contacting human body. The first temperature detection unit 11 has, for example, a rectangular shape with one side of about 1 mm to 2 mm, and consumes only a small current (for example, several mA or less) to measure a resistance value.

The heat absorption unit 12 includes, for example, a Peltier device. The heat absorption unit 12 has, for example, a rectangular shape with one side of about 1 mm to 2 mm. The heat absorption unit 12 includes a heat absorption surface that absorbs heat and a heat dissipation surface that is a surface on the opposite side of the heat absorption surface and dissipates heat absorbed by the heat absorption surface. The heat absorption unit 12 and the first temperature detection unit 11 are stacked, as shown in FIG. 2. The heat absorption surface of the heat absorption unit 12 contacts the first temperature detection unit 11.

When a heat absorption control unit 153 (to be described later) controls a current flowing into the heat absorption unit 12, the heat absorption unit 12 absorbs heat accumulated in the first temperature detection unit 11 to decrease the temperature of the first temperature detection unit 11. Note that the heat absorption unit 12 also consumes only a small current for heat absorption.

Similarly to the first temperature detection unit 11, the second temperature detection unit 13 includes a resistance temperature detector, such as a thermistor-type resistance temperature detector or platinum resistance temperature detector whose resistance value changes in accordance with a change in temperature, and a lead wire for causing a current to flow into the resistance temperature detector. For example, the second temperature detection unit 13 contacts the heat absorption surface of the heat absorption unit 12 to detect the temperature on the heat absorption surface of the heat absorption unit 12. Note that the second temperature detection unit 13 may contact the heat dissipation surface to detect the temperature on the heat dissipation surface.

The heat dissipation unit 14 is, for example, a metal plate. The heat dissipation unit 14 contacts the heat dissipation surface of the heat absorption unit 12 to dissipate heat absorbed by the heat absorption unit 12 from the first temperature detection unit 11. Note that if the pulsebeat measurement apparatus 1 is provided in a wearable device, a component with high heat conductivity used in the wearable device may be used as the heat dissipation unit 14.

Note that in this embodiment, the heat dissipation unit 14 is made to contact the heat absorption unit 12 that may be a Peltier device, and to dissipate heat absorbed by the heat absorption unit 12 from the first temperature detection unit 11. However, the present invention is not limited to this. For example, a cooling fan may be used as the heat absorption unit 12, instead of the Peltier device. In this case, the first temperature detection unit 11 may be made to contact the heat dissipation unit 14, and the cooling fan may dissipate heat from the heat dissipation unit 14.

The control unit 15 is formed by, for example, an electric circuit, and controls cooling of the first temperature detection unit 11 by the heat absorption unit 12 and measures the pulsebeat of the human body. The control unit 15 includes a first temperature measurement unit 151, a second temperature measurement unit 152, the heat absorption control unit 153, a specifying unit 156, a pulsebeat measurement unit 157, and an output unit 158.

The first temperature measurement unit 151 causes a current to flow into the first temperature detection unit 11, and measures a voltage (analog value) applied to the first temperature detection unit 11, thereby measuring the temperature of the human body. Since the resistance value of the first temperature detection unit 11 changes in accordance with the body temperature of the human body contacting the first temperature detection unit 11, the first temperature measurement unit 151 can measure the voltage applied to the first temperature detection unit 11, thereby measuring the temperature of the human body based on the voltage.

The first temperature measurement unit 151 converts the measured voltage value into a digital value by, for example, sampling the measured voltage value at a predetermined sampling frequency. Although a pulse period obtained from a pulse wave is several Hz, a band higher (for example, about 100 Hz) than the pulse period is required to detect a peak necessary for calculation of a pulse rate. Therefore, by setting a relatively high frequency (for example, 800 Hz) as a sampling frequency, the first temperature measurement unit 151 can function as a low-pass filter at the time of conversion into a digital value, and remove high-frequency noise included in the measured voltage value.

The voltage value converted into the digital value may include periodic noise caused by a commercial power supply or the like. The first temperature measurement unit 151 removes the periodic noise from the voltage value by, for example, calculating the moving average of voltage values converted into digital values during a predetermined period, approximating the waveform of the voltage values to a parabola, or applying a rectangular wave correlation filter that correlates the voltage value and a rectangular pulse formed from positive and negative pulse waves. Note that the first temperature measurement unit 151 removes noise by the above-described method. However, the present invention is not limited to this. Noise may be removed by using another noise removal method or combining a plurality of noise removal methods. The first temperature measurement unit 151 outputs, to the heat absorption control unit 153 and the specifying unit 156, a signal representing the voltage value from which the periodic noise has been removed. Note that the first temperature measurement unit 151 may convert, into a temperature, the voltage value converted into the digital value, based on the relationship between the voltage value and the temperature, and output a signal representing the temperature to the heat absorption control unit 153 and the specifying unit 156.

Similarly to the first temperature measurement unit 151, the second temperature measurement unit 152 measures a voltage value (analog value) applied to the second temperature detection unit 13, and converts the measured voltage value into a digital value. The second temperature measurement unit 152 removes periodic noise from the voltage value by calculating the moving average of voltage values converted into digital values during a predetermined period, and then outputs a signal representing the voltage value to the heat absorption control unit 153. Note that similarly to the first temperature measurement unit 151, the second temperature measurement unit 152 may convert, into a temperature, the voltage value converted into the digital value, and output a signal representing the temperature to the heat absorption control unit 153.

The heat absorption control unit 153 controls cooling of the first temperature detection unit 11 by controlling a current flowing into the heat absorption unit 12. The heat absorption control unit 153 includes a comparison calculation unit 154 and a current control unit 155. The comparison calculation unit 154 calculates the difference between the voltage value measured by the first temperature measurement unit 151 and the voltage value of the heat absorption unit 12 measured by the second temperature measurement unit 152.

Based on the difference calculated by the comparison calculation unit 154, the current control unit 155 controls a current flowing into the heat absorption unit 12 so that the temperature of the first temperature detection unit 11 becomes lower than the body temperature of the human body by a predetermined temperature (for example, 3°). For example, a table indicating the relationship between the difference in voltage value and the current value of the current flowing into the heat absorption unit 12 is stored in a storage unit (not shown) provided in the pulsebeat measurement apparatus 1. Then, with reference to the table, the current control unit 155 controls the current flowing into the heat absorption unit 12 based on the current value associated with the difference calculated by the comparison calculation unit 154. This causes the heat absorption unit 12 to decrease the temperature of the first temperature detection unit to a temperature lower than the body temperature of the human body by a predetermined temperature based on the temperature detected by the first temperature detection unit 11 and that detected by the second temperature detection unit 13. This allows the pulsebeat measurement apparatus 1 to forcibly absorb heat accumulated in the first temperature detection unit 11, thereby preventing the first temperature detection unit 11 from entering the thermal equilibrium state.

Note that in this embodiment, the heat absorption control unit 153 includes the comparison calculation unit 154 and the current control unit 155, and controls the current flowing into the heat absorption unit 12 so that the temperature of the first temperature detection unit 11 becomes lower than the body temperature of the human body by the predetermined temperature. However, the present invention is not limited to this. For example, the heat absorption control unit 153 may cause a constant current to flow into the heat absorption unit 12 all the time without including the comparison calculation unit 154. In this case, the pulsebeat measurement apparatus 1 need not include the second temperature detection unit 13 or the second temperature measurement unit 152.

The heat absorption control unit 153 may cause a current to intermittently flow into the heat absorption unit 12 in accordance with the period of a pulsebeat specified by the specifying unit 156 (to be described later). This can reduce power required to control cooling of the first temperature detection unit 11.

The specifying unit 156 specifies the period of a change in temperature caused by a pulsation of the human body based on the temperature of the human body detected by the first temperature detection unit 11. For example, if the first temperature detection unit 11 has a characteristic that the resistance value (voltage value) decreases along with a rise in temperature, the specifying unit 156 specifies a timing at which the body temperature becomes highest in accordance with a pulsation, by specifying a timing at which the voltage value output from the first temperature measurement unit 151 becomes low instantaneously. The specifying unit 156 specifies the period of a change in temperature caused by a pulsation of the human body by specifying the period of the timing.

The pulsebeat measurement unit 157 measures the pulsebeat of the human body from the period of a change in temperature caused by the pulsation specified by the specifying unit 156. More specifically, the pulsebeat measurement unit 157 considers, as an R-R interval, the period of the change in temperature caused by the pulsation specified by the specifying unit 156, and calculates a pulse rate based on the R-R interval, thereby measuring the pulsebeat of the human body.

The output unit 158 outputs the pulse rate measured by the pulsebeat measurement unit 157. The output unit 158 outputs the measured pulse rate to, for example, the wearable device or the like provided with the pulsebeat measurement apparatus 1. Thus, the wearable device or the like provided with the pulsebeat measurement apparatus 1 can display the pulse rate on a display unit provided in itself, cause a printer to print information including the pulse rate, and transmit information including the pulse rate to an external device.

As described above, the pulsebeat measurement apparatus 1 according to the first embodiment can suppress the first temperature detection unit 11 from entering the thermal equilibrium state by causing the heat absorption unit 12 to absorb heat, that is accumulated in the first temperature detection unit 11 by measuring the body temperature of the human body, to cool the first temperature detection unit 11, thereby detecting a change in temperature of the human body caused by a pulsation all the time.

Furthermore, by configuring the heat absorption unit 12 to include a Peltier device, heat of the first temperature detection unit 11 is absorbed forcibly. Thus, even if the heat capacity of the first temperature detection unit 11 becomes small as the pulsebeat measurement apparatus 1 is downsized, it is possible to absorb heat accumulated in the first temperature detection unit 11, thereby preventing the first temperature detection unit 11 from entering the thermal equilibrium state. Therefore, the pulsebeat measurement apparatus 1 can be downsized and operated stably.

Second Embodiment

A pulsebeat measurement apparatus 1 according to the second embodiment will be described. The pulsebeat measurement apparatus 1 according to the second embodiment is different from the first embodiment in that a heat insulation unit 16 is provided between a human body and a heat absorption unit 12. The remaining points are the same as in the first embodiment. The difference from the first embodiment will be described below. A description of the same points as in the first embodiment will be omitted appropriately.

Figure 4A:
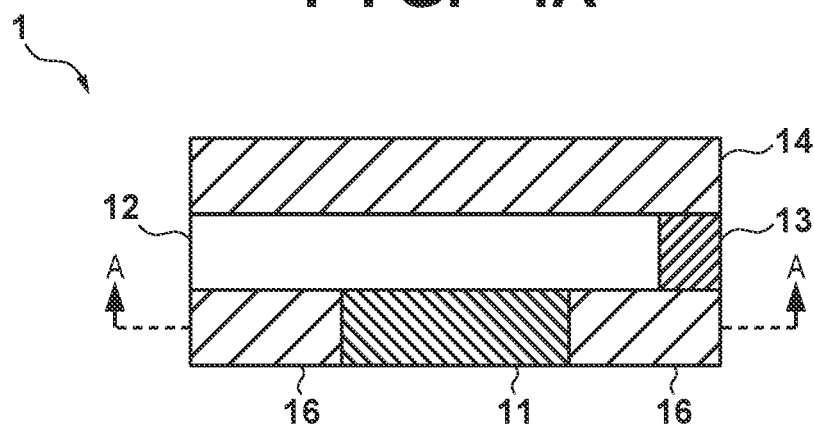
FIG. 4A is a view showing the arrangement of a pulsebeat measurement apparatus according to an embodiment.
Figure 4B:
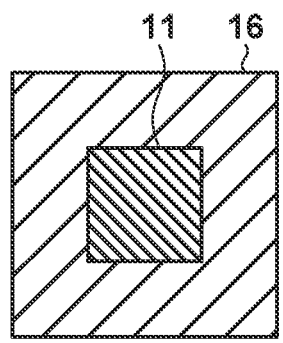
FIG. 4B is a view showing the arrangement of the pulsebeat measurement apparatus according to an embodiment.

FIGS. 4A and 4B are views showing the arrangement of the pulsebeat measurement apparatus 1 according to this embodiment. FIG. 4A is a side view showing the pulsebeat measurement apparatus 1. FIG. 4B is a schematic sectional view taken along a line A-A and showing the pulsebeat measurement apparatus 1. As shown in FIGS. 4A and 4B, the pulsebeat measurement apparatus 1 further includes the heat insulation unit 16 that suppresses transfer of heat between the human body and the heat absorption unit 12. The heat insulation unit 16 is arranged to surround a first temperature detection unit 11 in a direction orthogonal to the stacking direction of the first temperature detection unit 11 and the heat absorption unit 12. Thus, since the first temperature detection unit 11 and the heat insulation unit 16 exist between the human body and the heat absorption unit 12, it is possible to prevent the human body from contacting the heat absorption unit 12.

Third Embodiment

A pulsebeat measurement apparatus 1 according to the third embodiment will be described. For example, consider a case in which a finger of a user is placed on a first temperature detection unit 11 to measure the pulsebeat of the user. The first temperature detection unit 11 is an object having a rectangular shape with one side of about 1 mm to 2 mm, and is provided with a connecting portion that connects a resistance temperature detector and a lead wire by solder or the like. Therefore, a problem arises that when the finger of the user is placed on the first temperature detection unit 11, the finger unwantedly contacts the connecting portion to prevent the finger from contacting the resistance temperature detector sufficiently, and the first temperature detection unit 11 cannot detect the body temperature correctly. To solve this problem, the pulsebeat measurement apparatus 1 according to the third embodiment is different from the first embodiment in that the pulsebeat measurement apparatus 1 further includes a contact unit 17 which contacts the human body, and the first temperature detection unit 11 detects the temperature of the human body via the contact unit 17.

Figure 5:
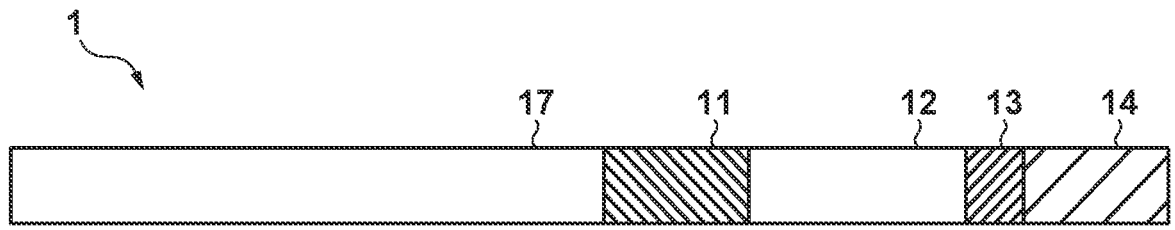
FIG. 5 is a side view showing a pulsebeat measurement apparatus according to an embodiment.

FIG. 5 is a side view showing the pulsebeat measurement apparatus 1 according to this embodiment. As shown in FIG. 5, the contact unit 17 is, for example, a metal plate with high heat conductivity or the like, and contacts the human body while being connected to the first temperature detection unit 11. An area of the contact unit 17 that can contact the human body is larger than an area of the resistance temperature detector of the first temperature detection unit 11 that can contact the human body.

If the human body (for example, the finger of the user for measuring the pulsebeat) contacts the contact unit 17, the first temperature detection unit 11 detects the temperature of the human body based on heat supplied from the human body via the contact unit 17. Thus, the first temperature detection unit 11 can accurately detect the temperature of the human body via the contact unit 17 that has a relatively large contact area to readily contact the human body.

As shown in FIG. 5, the contact unit 17 is connected to one end of the first temperature detection unit 11 and a heat absorption unit 12 is connected to the other end on the opposite side of the one end of the first temperature detection unit 11. This can reduce the possibility that the human body contacts the heat absorption unit 12 when contacting the contact unit 17. Note that in the example shown in FIG. 5, a heat dissipation unit 14 contacts a second temperature detection unit 13. However, another portion (not shown) of the heat dissipation unit 14 contacts the heat absorption unit 12.

The present invention has been described above using the embodiments. However, the present invention is not limited to the technical scope described in the embodiments. Various modifications or improvements can be made for the embodiments, as is apparent to those skilled in the art. In particular, a detailed embodiment of distribution/integration of devices is not limited to that illustrated, and all or some of the devices can be functionally or physically distributed/integrated in an arbitrary unit in accordance with various additions or a functional load.

The invention claimed is:

1. A pulsebeat measurement apparatus comprising:
a first temperature detector configured to detect a temperature of a human body;
a specifying unit configured to specify a period of a temperature change caused by a pulsation of the human body based on the detected temperature;
a pulsebeat measurement unit configured to measure a pulsebeat of the human body based on the specified period of the temperature change;
a heat absorber configured to absorb heat of the first temperature detector; and
a second temperature detector configured to detect a temperature of the heat absorber,
wherein the heat absorber is further configured to decrease a temperature of the first temperature detector to be lower than a body temperature of the human body by a predetermined temperature by absorbing heat of the first temperature detector based on the temperature detected by the first temperature detector and the temperature detected by the second temperature detector.

2. The pulsebeat measurement apparatus according to claim 1, further comprising:
a contact unit contacting the human body and connected to the first temperature detector,
wherein the first temperature detector is further configured to detect the temperature of the human body based on heat supplied from the human body via the contact unit.

3. The pulsebeat measurement apparatus according to claim 2, wherein
the contact unit is connected to one end of the first temperature detector, and
the heat absorber is connected to another end of the first temperature detector.

4. The pulsebeat measurement apparatus according to claim 1, further comprising a heat insulator configured to suppress transfer of heat between the human body and the heat absorber.

5. The pulsebeat measurement apparatus according to claim 4, wherein
the first temperature detector and the heat absorber are stacked, and the heat insulator is arranged to surround the first temperature detector in a direction orthogonal to a stacking direction of the first temperature detector and the heat absorber.

6. The pulsebeat measurement apparatus according to claim 1, wherein the heat absorber includes a Peltier device.

* * * * *